United States Patent

Hugl et al.

[11] Patent Number: 4,962,040
[45] Date of Patent: Oct. 9, 1990

[54] 2-HYDRAZONO-4,6-DINITROBENZ-THIAZOLONES USEFUL TO FORM DYESTUFFS AND AS COLOR FORMERS FOR DETECTING PEROXIDE

[75] Inventors: Herbert Hugl, Bergisch Gladbach; Aloysius Engel, Leverkusen; Klaus Wehling, Wuppertal, all of Fed. Rep. of Germany

[73] Assignee: Bayer Aktiengesellschaft, Leverkusen, Fed. Rep. of Germany

[21] Appl. No.: 392,520

[22] Filed: Aug. 10, 1989

Related U.S. Application Data

[63] Continuation of Ser. No. 55,098, May 28, 1987, abandoned.

[30] Foreign Application Priority Data

Jun. 4, 1986 [DE] Fed. Rep. of Germany ....... 3618752

[51] Int. Cl.$^5$ .................... G01N 31/14; C09B 29/045; D06P 1/04; D06P 1/06
[52] U.S. Cl. ................. 436/135; 252/408.1; 422/56; 423/582; 423/584; 534/578; 534/586; 534/733; 534/768; 534/769; 534/778; 534/788; 534/782; 548/161; 548/164; 568/558; 568/568; 568/570; 568/571
[58] Field of Search .............. 534/578, 586, 788; 548/161; 422/56; 436/135; 252/408.1; 423/582, 584; 568/558, 568, 570, 571

[56] References Cited

U.S. PATENT DOCUMENTS 3,153,031  10/1964  Alicot et al. ................. 534/578 X
4,089,747   5/1978  Bruschi ......................... 436/135 X

*Primary Examiner*—Floyd D. Higel
*Attorney, Agent, or Firm*—Sprung Horn Kramer & Woods

[57] ABSTRACT

2-Hydrazono-4,6-dinitrobenzthiazolones of the formula

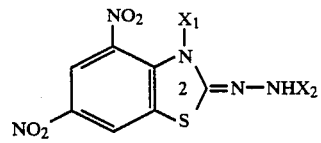

in which
$X_1$ represents hydrogen, $C_1$–$C_4$-alkyl, $C_1$–$C_4$-hydroxyalkyl, $C_1$–$C_4$-sulphoalkyl or $C_1$–$C_4$-sulphatoalkyl, and
$X_2$ represents hydrogen or —$SO_2X_3$, where
$X_3$ may represent hydrogen, $C_1$–$C_8$-alkyl or optionally substituted aryl and
$X_1$ also represents a double bond between the cyclic nitrogen atom and the carbon atom 2 according to the formula II below:

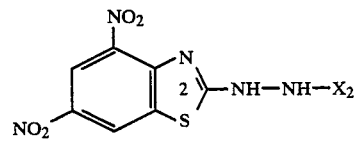

where $X_2$ has the meaning specified under the above formula.

These hydrazones may be employed in the preparation of azo dyestuffs and as color formers for detecting of biological substances, and in the determination of $H_2O_2$.

1 Claim, No Drawings

2-HYDRAZONO-4,6-DINITROBENZTHIAZO-LONES USEFUL TO FORM DYESTUFFS AND AS COLOR FORMERS FOR DETECTING PEROXIDE

This is a continuation of application Ser. No. 055,098, filed May 28, 1987, now abandoned.

It has been found that 2-hydrazono-4,6-dinitrobenzthiazolones are suitable for the preparation of valuable azo dyestuffs and may furthermore be employed as color formers for detecting substances, particularly in the determination of $H_2O_2$.

The present invention relates to 2-hydrazono-4,6-dinitrobenzthiazolones of the formula (I)

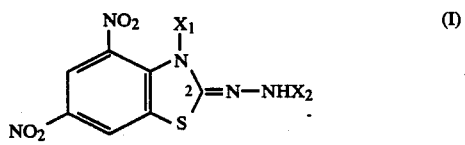

in which $X_1$ represents hydrogen, $C_1-C_4$-alkyl, $C_1-C_4$-hydroxyalkyl, $C_1-C_4$-sulphoalkyl or $C_1-C_4$-sulphatoalkyl, and $X_2$ represents hydrogen or $-SO_2X_3$, where $X_3$ may represent hydrogen, $C_1-C_8$-alkyl or optionally substituted aryl.

$X_1$ preferably represents hydrogen or the methyl group.

$X_1$ preferably also represents a double bond between the cyclic nitrogen atom and the carbon atom 2 according to the formula II below:

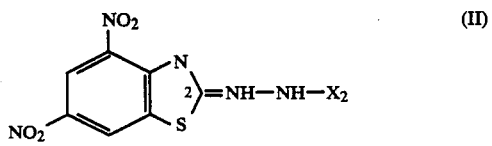

where $X_2$ has the meaning specified under the general formula I.

The hydrazones may also be employed in protected form, for example in the form of aliphatic hydrazones of the formula III

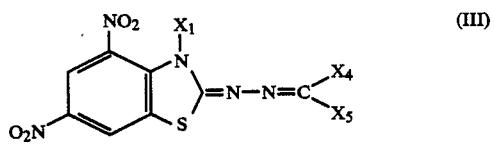

in which $X_4$ and $X_5$, independently of one another, denote $C_1-C_8$-alkyl, and $X_1$ has the meaning specified above in the general formula I.

The present invention further relates to the use of 2-hydrazono-4,6-dinitrobenzthiazolones of the general formula I for the preparation of azo dyestuffs and as color formers for detecting substances, particularly in the determination of $H_2O_2$. In the context of the present invention, color formers are taken to mean those substances which form a dyestuff after oxidation using a suitable coupling component. The present invention thus also generally relates to the area of diagnostic tests and, here, particularly those tests which concern the qualitative and quantitative determination of oxidizable biological substances, for example lactic acid, glucose, cholesterol, uric acid, creatinine, GPT or also glycerol and ketone bodies. In such tests, these biological substances are usually oxidized by a specific oxidase. An $H_2O_2$-dependent oxidation of the color former according to the invention then occurs by means of the catalytic action of a peroxidase or peroxidatively-active substance, such as, for example, hemoglobin or methemoglobin. The oxidation product is then able to react with a suitable coupling component with formation of a dyestuff. The 4,6-dinitrobenzthiazol-2-one according to the invention are also excellently suited for the detection of peroxidase or a peroxidatively-active substance. Such detection occurs with utilization of the oxidation and coupling reactions described above, $H_2O_2$ or another peroxide, for example cumene hydroperoxide, strontium peroxide or 2,5-dimethylhexane 2,5-dihydroperoxide, being employed as oxidant.

A further component of the present invention comprises that the color formers according to the invention, 2-hydrazono-4,6-dinitrobenzthiazolones according to the general formula (I), either in solution or in a device, for example as reagent, in a test strip or in an analytical element, cause a visible color change of the sample to be investigated.

2-Hydrazono-4,6-dinitrobenzthiazolones can be obtained in good yields by the following process.

2-Amino-4,6-dinitrobenzthiazole, obtained by nitration of 2-amino-benzthiazole, is reacted with hydrazine hydrate in a suitable solvent. 2-Ethoxyethanol, for example, is employed as solvent. The reaction is preferably carried out with supply of heat, particularly preferably at 70° C. to 150° C., excellent yields being produced when working at the boiling point of the mixture (about 128°–130° C.).

Hydrazine hydrate is preferably employed in 100% purity. The reaction duration is about 1 hour, and a continuous process procedure is also possible. The reaction mixture, after cooling, is transferred into an acidified, aqueous solution. An aqueous glacial acetic acid solution may be employed to good effect. The reaction product is separated off, preferably washed, and dried.

It has been found that the new 2-hydrazono-4,6-dinitrobenzthiazolones may be oxidized and then used for the preparation of azo dyestuffs with a large number of coupling components. Azo dyestuffs prepared in this fashion may be used to particularly good effect in the dyeing of natural and synthetic fibers, woven fabrics or knitted fabrics.

The preparation of azo dyestuffs from 2-hydrazono-4,6-dinitrobenzthiazolones by oxidative coupling represents a simple and economically very important process.

Aromatics which are accessible to electrophilic attack, such as, for example, the compounds below, may be employed according to the invention as coupling components for the oxidative coupling:

COUPLING COMPONENTS

1.

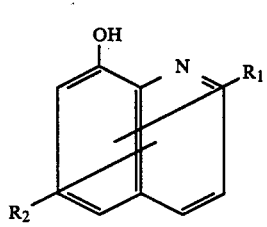

$R_1$ and $R_2$ may be identical or different and denote hydrogen, $C_1$-$C_4$-alkyl, $C_1$-$C_4$-alkoxy, phenyl, fluorine, chlorine, bromine or iodine, preferably hydrogen.

2.

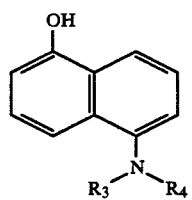

$R_3$ and $R_4$ may be identical or different and denote hydrogen, —$C_2H_4$—O—$R_5$, —$C_2H_4$—O—CO—$R_5$, or $C_1$-$C_4$-alkyl, where $R_5$ represents $C_1$-$C_4$-alkyl or phenyl, and preferably denotes hydrogen.

3.

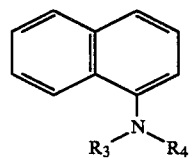

$R_3$ and $R_4$ have the same meaning as specified under 2., preferably hydrogen or ethyl.

4.

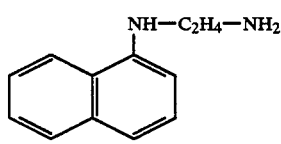

5.

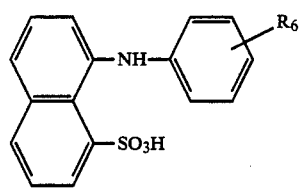

$R_6$ denotes hydrogen or methyl.

6.

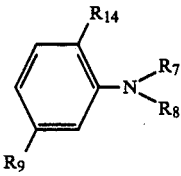

$R_7$ and $R_8$ may be identical or different and denote: hydrogen, $C_1$-$C_8$-alkyl which is optionally substituted by sulpho, sulphato, hydroxyl, cyano, halogen, $C_1$-$C_4$-alkoxy, —OCOR$_5$, —COOR$_5$, OCONHR$_5$, phenyl or sulphophenyl, and also denote $C_3$-$C_6$-alkenyl. $R_5$ here represents $C_1$-$C_4$-alkyl or phenyl. $R_7$ and $R_8$ preferably denote hydrogen, ethyl, hydroxyethyl, cyanoethyl, propyl, butyl, acetoxyethyl, methoxycarbonylethyl, ethoxycarbonylethyl, methylaminocarbonyloxyethyl, phenylaminocarbonyloxyethyl, benzyl, phenethyl and sulphobenzyl.

$R_9$ denotes hydrogen, $C_1$-$C_4$-alkyl, $C_1$-$C_4$-alkoxy, hydroxyl, —NHCOR$_5$ or —NHSO$_2$R$_5$, where $R_5$ has the above-mentioned meaning.

$R_9$ preferably denotes hydrogen, methyl, NHCOCH$_3$ and NHSO$_2$CH$_3$.

$R_{14}$ denotes hydrogen, halogen, $C_1$-$C_4$-alkyl, $C_1$-$C_4$-alkoxy or $C_2$-$C_8$-alkoxyalkyl, preferably hydrogen, chlorine, methyl or methoxy.

7.

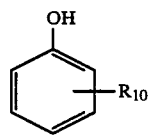

$R_{10}$ denotes hydrogen, methyl, hydroxyl or chlorine, preferably methyl or hydroxyl.

8.

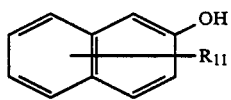

$R_{11}$ denotes hydrogen, COOH or SO$_3$H, preferably

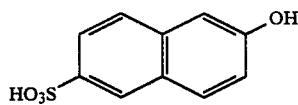

or

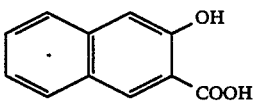

9.

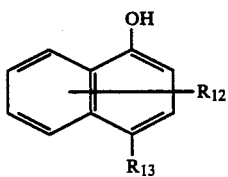

R$_{12}$ denotes hydrogen or SO$_3$H, preferably hydrogen;
R$_{13}$ denotes hydrogen or O—CH(CH$_3$)—COOH.
10.

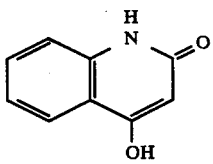

11.

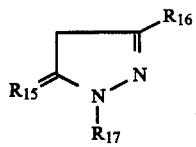

R$_{15}$ denotes O or NH.
R$_{16}$ denotes CH$_3$, COOH or NH$_2$, preferably methyl.
R$_{17}$ denotes C$_2$–C$_8$-alkyl, H, phenyl, sulphophenyl, preferably phenyl of sulphophenyl
12.

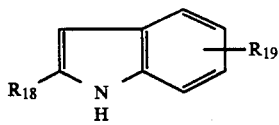

R$_{18}$ denotes CH$_3$ or phenyl, preferably methyl.
R$_{19}$ denotes H or SO$_3$H.
13.

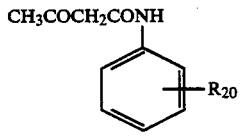

R$_{20}$ denotes H, OCH$_3$, Cl or CH$_3$, preferably OCH$_3$.
14.

R$_{21}$ and R$_{22}$ may be identical or different and denote CN or COOC$_2$H$_5$, preferably CN.
15.

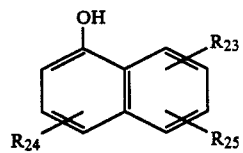

R$_{23}$ denotes NH$_2$ or OH.
R$_{24}$ denotes hydrogen or SO$_3$H.
R$_{25}$ denotes H or SO$_3$H, preferably

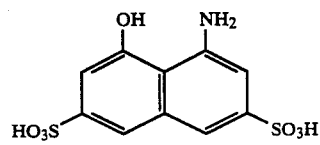

or

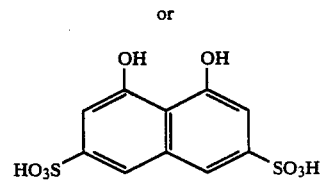

or

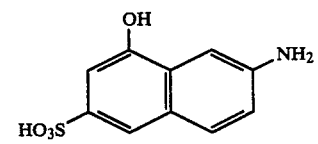

16.

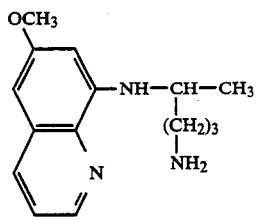

All coupling components mentioned are valuable both for the preparation of azo dyestuffs for dyeing textile fibers and for carrying out diagnostic tests by the process according to the invention. Very particularly high-quality dyestuffs for dyeing synthetic fibers are obtained when using the coupling components of the formula as specified under 6.

The oxidative coupling for the preparation of textile dyestuffs is carried out in a fashion which is known per se. Inorganic salts, such as periodates, borates, ferrates and peroxodisulphates are used as oxidants: sodium metaperiodate, potassium hexacyanoferrate and potassium bromate are particularly suitable.

The dyestuffs thus obtained are also accessible via diazotization of 2-amino-4,6-dinitrobenzthiazole and coupling, for example by the process specified in U.S. Pat. No. 3,057,848.

The present invention furthermore relates to a process for the determination of oxidizable biological substances. In the context of the present invention, such substances are taken as including those which are oxidized with generation or liberation of H$_2$O$_2$. This reaction preferably proceeds in an aqueous medium.

In order to carry out this detection process, a sample of the oxidizable biological substance to be analyzed is brought into contact with a suitable oxidase and a substance having peroxidative activity, the 2-hydrazono-4,6-dinitrobenzthiazolones as colour formers, and a coupling component. The invention furthermore relates to analytical elements and to reagents for carrying out this process; if appropriate, such reagents can contain further substances, such as, for example, buffers, wetting agents and stabilizers. Suitable buffers are borate, citrate, phosphate, glutarate, carbonate or tris amine buffers.

The qualitative detectability and quantitative determinability of H$_2$O$_2$ and substances which react with generation or liberation of H$_2$O$_2$ is very important in many areas. An example which may be mentioned is the detection and determination of H$_2$O$_2$ which is formed during the enzymatic determination of substances, for example glucose, cholesterol, uric acid and many others, by the activity of enzymes, for example glucose oxidase, cholesterol oxidase and uricase, in the presence of oxygen. The occurrence, or even the quantitative amount, of an enzyme substrate present in a sample can be determined from the amount of H$_2$O$_2$ generated.

Known reagents for the detection and/or quantitative determination of H$_2$O$_2$ which is generated in such systems generally contain a substance having peroxidative activity, for example peroxidase or peroxidase-type substances, such as, for example, hemoglobin, or furthermore a substance which undergoes detectable change in the presence of H$_2$O$_2$. Peroxidase is an enzyme which catalyzes the oxidation of the color former by H$_2$O$_2$. The preparation of peroxidases is generally known, and such enzymes are commercially available. The oxidative coupling for the detection of H$_2$O$_2$ is already known, cf. H. U. Bergmeyer, Methods of Enzymatic Analysis, 3rd Ed., Vol I, 1984, p. 216. Surprisingly, it has been found that 2-hydrazono-4,6-dinitrobenzthiazolones are very well suited as color formers in such a reaction.

The presence or the formation of H$_2$O$_2$, the substance with peroxidative activity and the color former, and also color coupler, is important for carrying out such a detection reaction. This mixture causes the color change in the sample to be investigated.

The present invention permits the determination of very low concentrations of H$_2$O$_2$. A buffered reagent or reagent system having a certain composition is preferably employed. The color reaction is advantageously very sensitive and also linear over a large concentration range, so that at least semi-quantitative statements can be made in this range by simple reading of, for example, reagent strips. This vividly illustrates the immense advantage of the present invention. The hue formed is color-stable for a very long time and allows reading over a broad time span. Furthermore, combination of different coupling components allows dyeings in different shades to be achieved. This is particularly true for the long-wave region, for which only a few chromogens have been available hitherto. This allows spectral interferences with hemoglobin and bilubin or turbidity influences to be substantially avoided.

The color reaction for detection of H$_2$O$_2$ or substances which liberate H$_2$O$_2$ is based on the following equation, in clarified form:

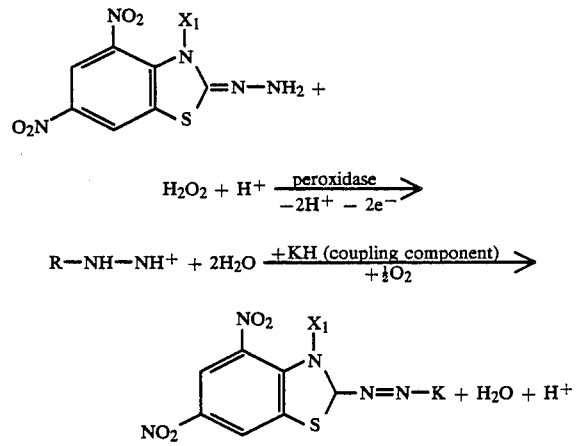

The determination of the dyestuff density as a quantitative measure of the concentration of H$_2$O$_2$ is carried out by conventional methods, for example optically by means of spectrophotometers, preferably reflectometers, or by comparison using color scales, color cards or using standard solutions.

The compositions according to the invention may furthermore contain buffers or substances which permit the adjustment of the pH into an acid region. The adjustment of the pH into such an acid region need not necessarily be carried out, but is preferred, particularly in the use according to the invention as a diagnostic reagent or element; an acid adjustment is not necessary for the use, likewise according to the invention, for the preparation of azo dyestuffs.

The reagents according to the invention may be present in the form of solutions to which only the sample to be investigated need be added, or in the form of a test kit, to which the sample is added shortly before the determination.

In a further advantageous embodiment of the invention, analytical elements are employed. Such elements can be prepared, for example, by impregnation of suitable absorbent substances, for example absorbent papers and solutions of the reagents.

Such elements may comprise several different layers. The known methods for the preparation of test strips can be employed broadly in the present invention.

The determination reagents according to the invention may be present in the form of dry mixtures, which may be converted, for example, into diagnostic solutions by addition of water.

The subject-matter of the present invention is illustrated in greater detail by the examples below.

EXAMPLE 1

Preparation of the Hydrazine of the Formula

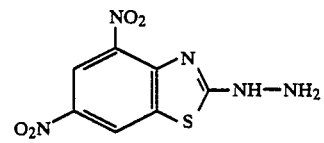

24.0 g of amino-4,6-dinitrobenzthiazole are heated to boiling for 1 hour in 200 ml of 2-ethoxyethanol with 20 ml of hydrazine hydrate (100% purity). After cooling to room temperature, the reaction mixture is poured into a mixture of 750 ml of water and 20 ml of glacial acetic acid, stirred for 1 hour, filtered off under suction, washed with water and dried. 21.0 g of 2-hydrazino-4,6-dinitrobenzthiazole are obtained. Melting point 210°-214° C. (decomposition). After recrystallization from 2-methoxyethanol. Melting point 216°-217° C. (decomposition).

EXAMPLE 2

A total of 18.5 g of 2-hydrazino-4,6-dinitrobenzthiazole, 15.0 g of N,N-dibutylaniline and 15.5 g of sodium metaperiodate are added in 10 portions over 4 hours to 500 ml of glacial acetic acid with stirring at room temperature. The mixture is subsequently stirred for a further 5 hours, water is added, and the product is filtered off under suction, recrystallized from dimethylformamide and dried. The dyestuff has the structure

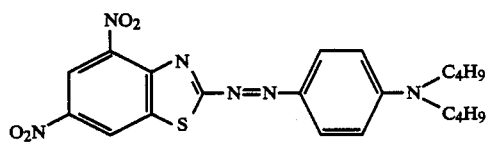

and dyes polyester fibers blue with good fastnesses.

The dyestuffs shown in the table below may be obtained in an analogous or similar working procedure in good yield:

Dyestuffs of the formula

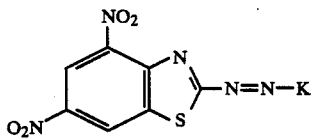

| Example No. | K | Shade on polyester |
|---|---|---|
| 3 | Ph-N(CH₂—CH₂—CN)(CH₂—CH₂—OCOCH₃) | red-violet |
| 4 | 2-Cl-C₆H₄-NHCH₂CH₂CN | red-bordeaux |
| 5 | Ph-N(CH₂CH₂OCONHPh)₂ | blueish bordeaux |
| 6 | 3-CH₃-C₆H₄-N(C₂H₅)(CH₂CH₂OCONHCH₃) | reddish dark blue |

Optical Properties of the Reagents for Detecting Peroxide

The following procedure is followed for determinating the optical properties of the peroxide indicators:

2-Hydrazono-4,6-dinitrobenzthiazoles and the appropriate coupling components are prepared as concentrated stock solutions (2–10 mmol/l) in 0.1M buffer. If a substance does not dissolve quantitatively, it is dissolved using buffer/DMF or buffer/DMSO mixtures. These solutions are subsequently mixed and further diluted with the necessary buffer solution, and the pH is checked. 10 μl of peroxidase are added to 500 μl of this solution in a cell, the extinction of the blank value is measured, and the reaction is then started by adding 10 μl of freshly prepared peroxide solution (1–5 mmol/l). After 5 minutes, the extinction is measured again and the blank value is separated.

The peroxide concentration employed is checked by measuring the extinction at 240 nm. (5 mmol/l of $H_2O_2$ = 0.25 $E_{240}$). The following concentrations were used in the test batch for the indicators described below:

| | |
|---|---|
| hydrazono-4,6-dinitrobenzthiazolone | 5 mmol/l |
| coupling component | 5 mmol/l |
| peroxidase | 5 kU/l |
| citrate buffer, pH 5.0 | 100 mmol/l |
| peroxide test solution: | 5 mmol/l |

The following extinction differences were measured at the absorption maxima specified after a reaction time of 5 minutes:

| Example No. | K | $\lambda_{max}$ [nm] | ΔE |
|---|---|---|---|
| 7 | 3-NHCOCH₃-C₆H₄-N(C₂H₅)(CH₂-C₆H₄-3-SO₃H) | 570 | 1.393 |
| 8 | 3-NHCOCH₃-C₆H₄-N(C₂H₄OH)₂ | 590 | 1.573 |
| 9 | 3-CH₃-C₆H₄-N(C₂H₅)(CH₂-C₆H₄-SO₃H) | 615 | 1.638 |
| 10 | 3-NHCOCH₃-C₆H₄-N(C₂H₅)₂ | 585 | 0.834 |
| 11 | 3-CH₃-C₆H₄-N(C₂H₅)(C₂H₄OH) | 615 | 1.841 |
| 12 | 8-hydroxyquinoline | 590 | 1.700 |

-continued

| Example No. | K | λ_max [nm] | ΔE |
|---|---|---|---|
| 13 | 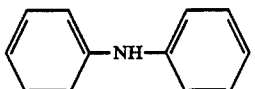 | 554 | 0.400 |
| 14 | 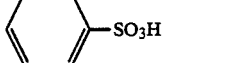 | 620 | 0.200 |
| 15 | 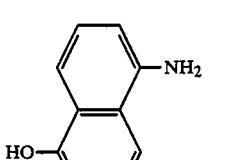 | 510 | 2.240 |
| 16 |  | 508 | 0.065 |
| 17 |  | 508 | 5.200 |
| 18 | 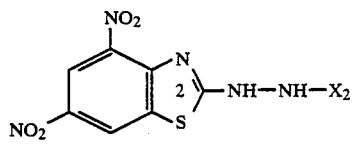 | 658 | 13.500 |
| 19 |  | 580 | 0.390 |
| 20 |  | 592 | 0.100 |

We claim:

1. In a process for the determination of hydrogen peroxide in aqueous liquids, in which process a sample of the liquid to be analyzed is brought into contact with a substance having peroxidative activity and a color former which reacts to form a dyestuff in the presence of hydrogen peroxide and the substance having peroxidative activity and a coupling component, the improvement comprising the use of a 2-hydrazono,-4,6-dinitrobenzthiazolone of the formula in which
X₂ represents hydrogen.

* * * * *